United States Patent
Patra et al.

(10) Patent No.: US 12,023,507 B2
(45) Date of Patent: Jul. 2, 2024

(54) SYSTEMS AND METHODS FOR FLEXIBLE, HIGH-DENSITY OPTO-ELECTRONIC ARRAYS

(71) Applicant: Lawrence Livermore National Security, LLC, Livermore, CA (US)

(72) Inventors: Susant Patra, Brentwood, CA (US); Razi-Ul Muhammad Haque, San Francisco, CA (US); Komal Kampasi, San Francisco, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 756 days.

(21) Appl. No.: 16/591,874

(22) Filed: Oct. 3, 2019

(65) Prior Publication Data
US 2021/0101013 A1    Apr. 8, 2021

(51) Int. Cl.
| | |
|---|---|
| A61N 5/06 | (2006.01) |
| A61N 1/36 | (2006.01) |
| A61N 1/372 | (2006.01) |
| F21V 8/00 | (2006.01) |
| G02B 6/12 | (2006.01) |
| G02B 6/28 | (2006.01) |
| G02B 6/42 | (2006.01) |
| G02B 6/43 | (2006.01) |
| H01S 5/183 | (2006.01) |
| A61B 18/00 | (2006.01) |

(Continued)

(52) U.S. Cl.
CPC ..... *A61N 1/37247* (2013.01); *A61N 1/36125* (2013.01); *A61N 1/37205* (2013.01); *A61N 5/0601* (2013.01); *A61N 5/0622* (2013.01); *G02B 6/0008* (2013.01); *G02B 6/12* (2013.01); *G02B 6/4293* (2013.01); *G02B 6/43* (2013.01); *H01S 5/183* (2013.01); *A61B 2018/00636* (2013.01); *A61B 2562/028* (2013.01); *A61B 2562/04* (2013.01); *A61B 2562/228* (2013.01); *A61N 5/067* (2021.08); *G02F 1/0018* (2013.01)

(58) Field of Classification Search
None
See application file for complete search history.

(56) References Cited

U.S. PATENT DOCUMENTS

| | | | |
|---|---|---|---|
| 9,907,496 B1 * | 3/2018 | Okandan | A61B 5/1459 |
| 2011/0081118 A1 * | 4/2011 | Uemura | G02B 6/4283 |
| | | | 385/88 |

(Continued)

FOREIGN PATENT DOCUMENTS

| | | | | |
|---|---|---|---|---|
| WO | WO-2011057276 A2 * | 5/2011 | | A61B 5/04001 |
| WO | WO-2019035876 A1 * | 2/2019 | | A61N 5/0601 |

*Primary Examiner* — Erica S Lee
(74) *Attorney, Agent, or Firm* — HARNESS, DICKEY & PIERCE, P.L.C.

(57) ABSTRACT

An opto-electronic probe system is disclosed. The probe system has a probe element including at least one microelectrode, with the probe element being implantable in tissue of an anatomy to receive electrical signals generated within the anatomy. A subsystem is included for at least one of generating excitation signals to be used in stimulating the anatomy, or for receiving electrical signals received from the anatomy. An interface portion is included which is in communication with the subsystem for communicating at least one of electrical signals or optical signals indicative of the electrical signals received by the microelectrode.

23 Claims, 7 Drawing Sheets

(51) Int. Cl.
 *A61N 5/067* (2006.01)
 *G02F 1/00* (2006.01)

(56) References Cited

U.S. PATENT DOCUMENTS

| | | | | |
|---|---|---|---|---|
| 2014/0353713 | A1* | 12/2014 | Kuh | H01L 31/022408 |
| | | | | 438/94 |
| 2016/0367836 | A1* | 12/2016 | Kampasi | G02B 6/0008 |
| 2017/0168235 | A1* | 6/2017 | Zhang | G02B 6/4257 |
| 2019/0351219 | A1* | 11/2019 | Mercanzini | A61N 1/0534 |

* cited by examiner

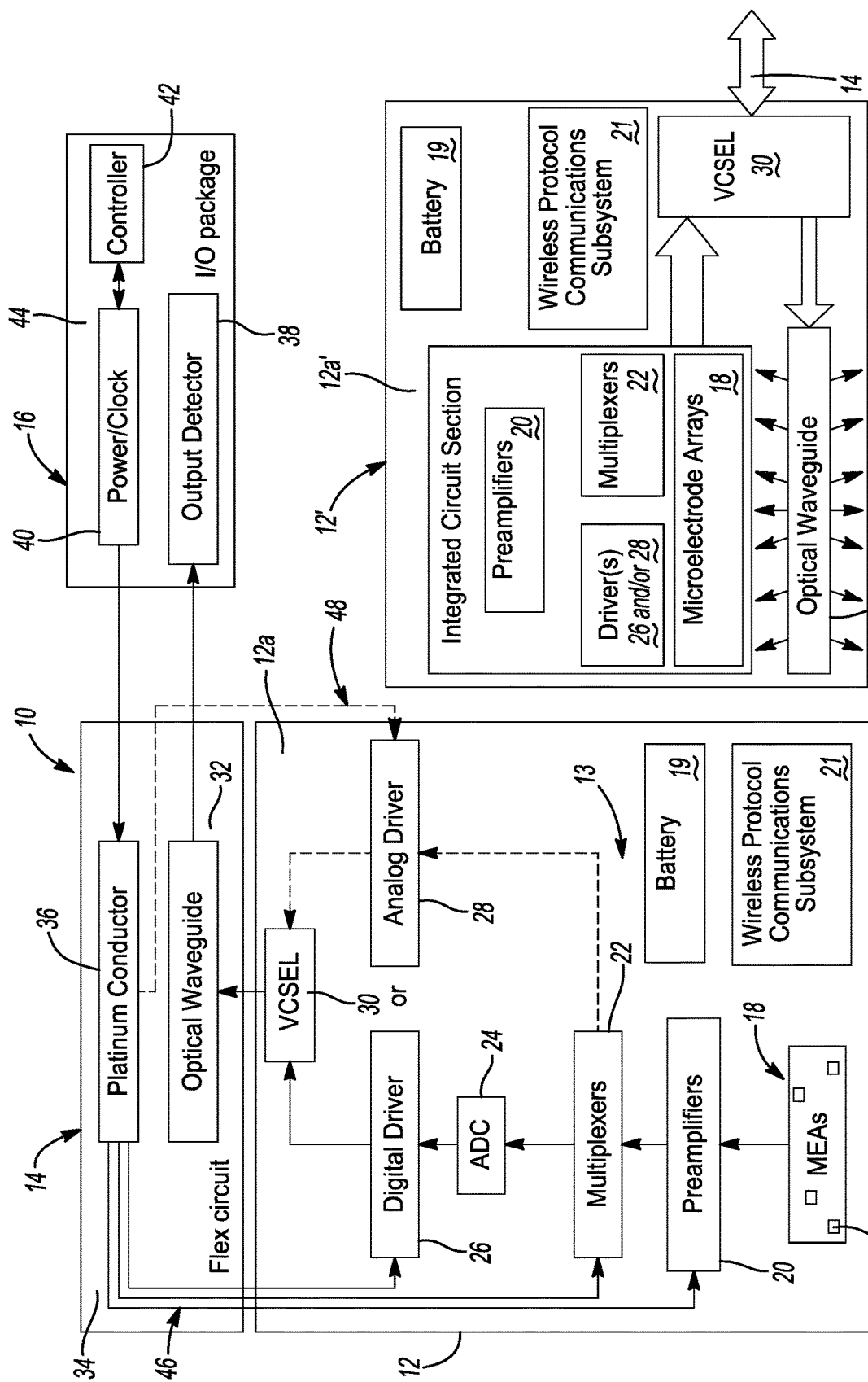

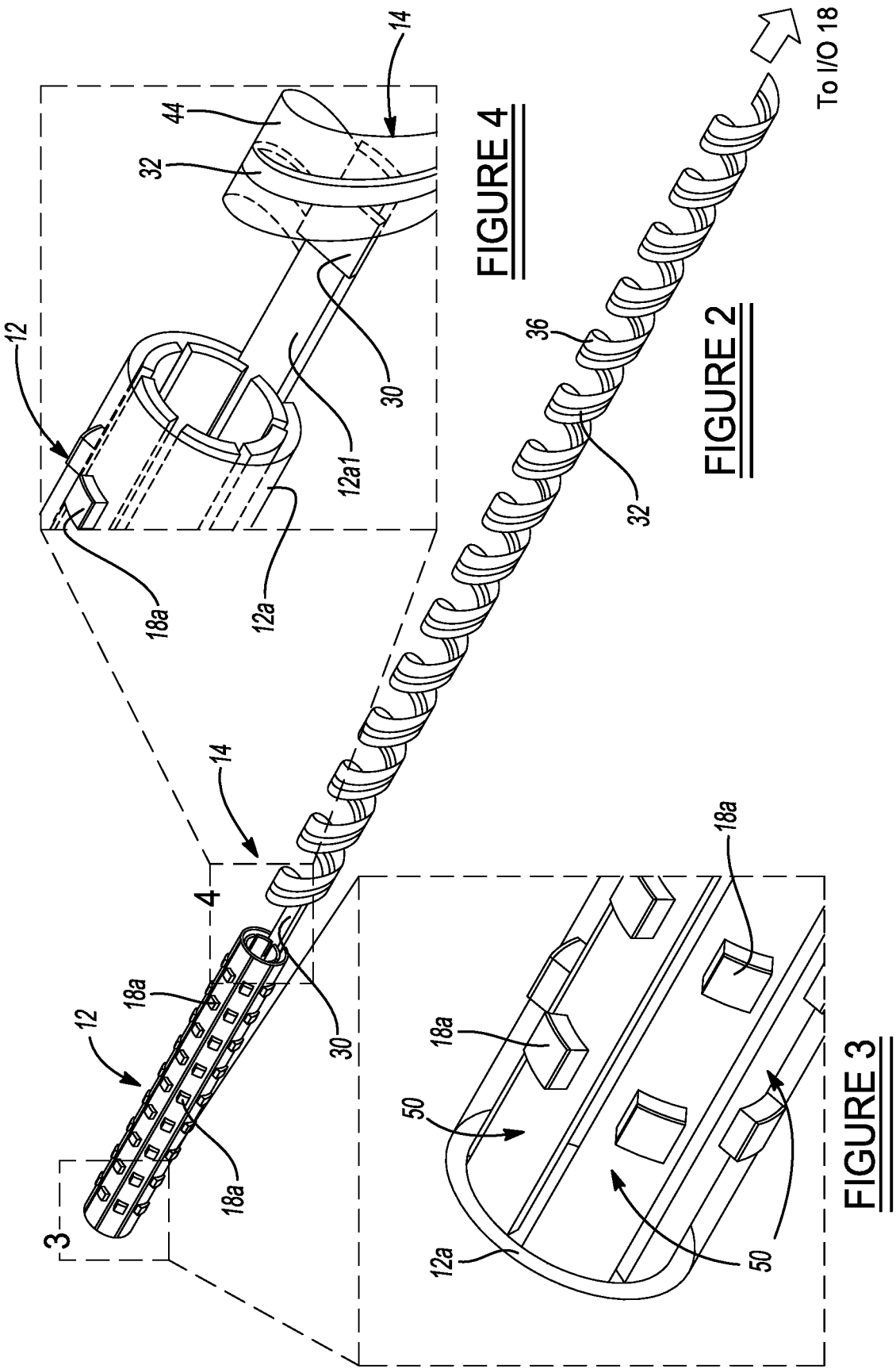

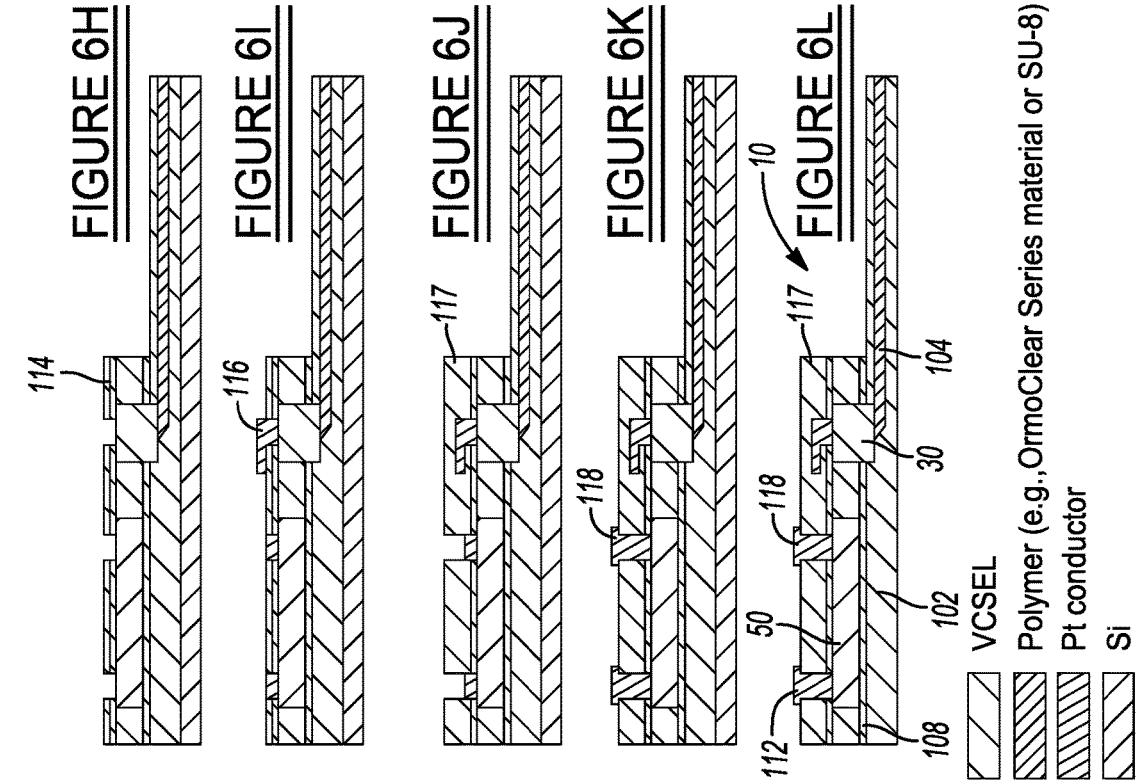
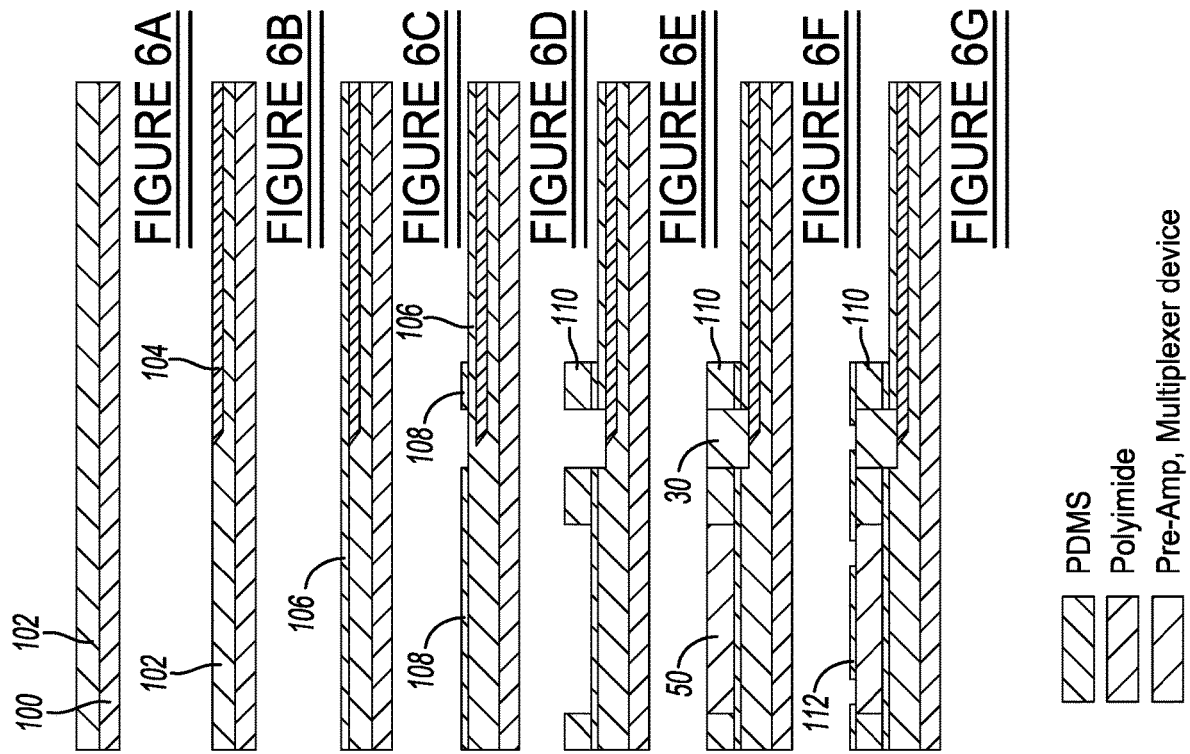

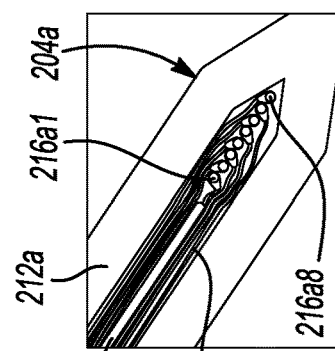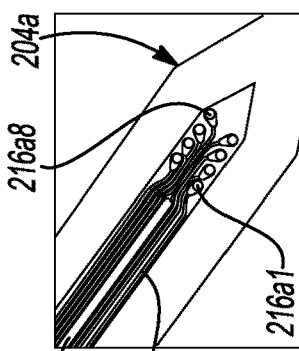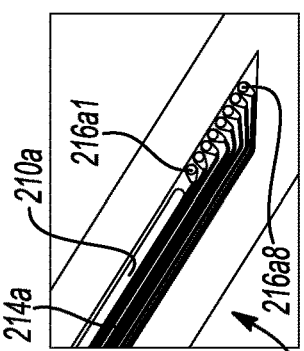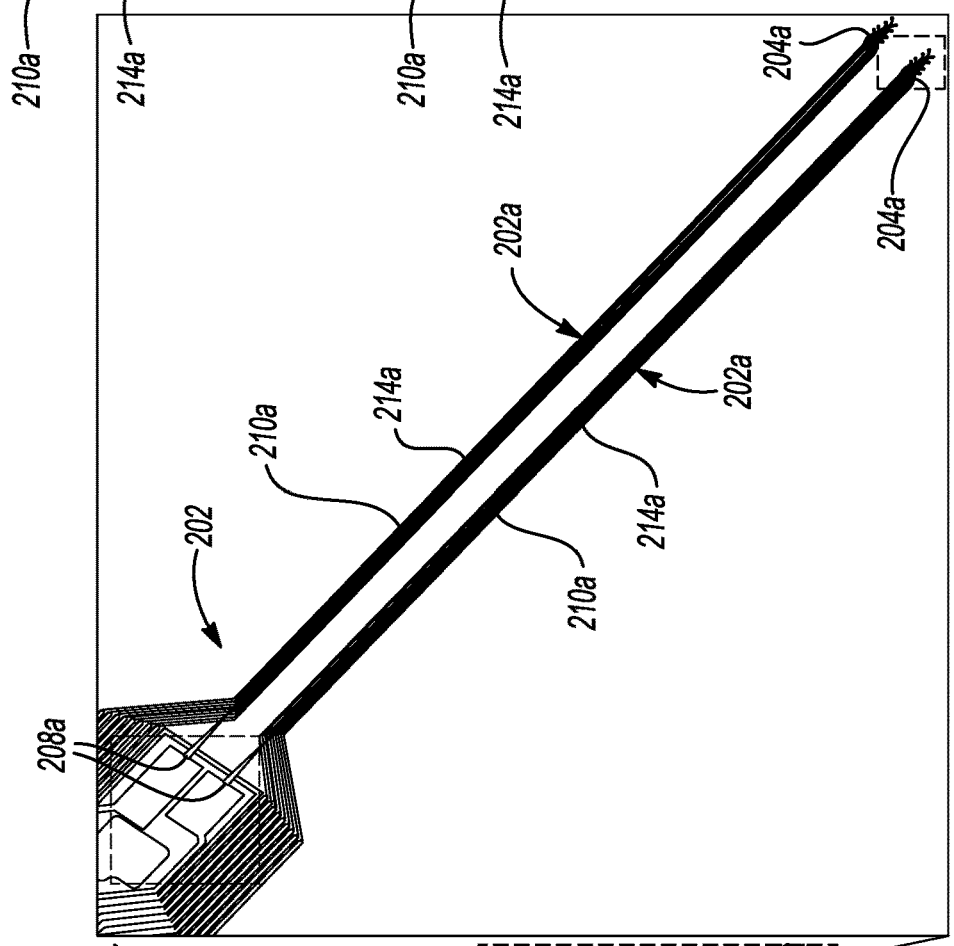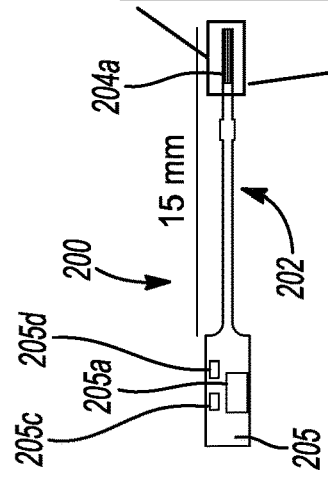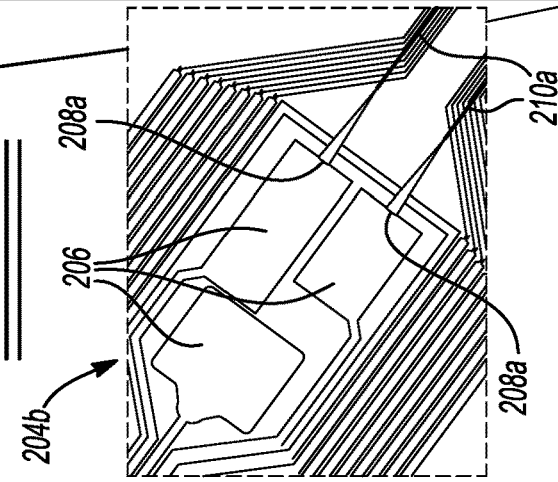

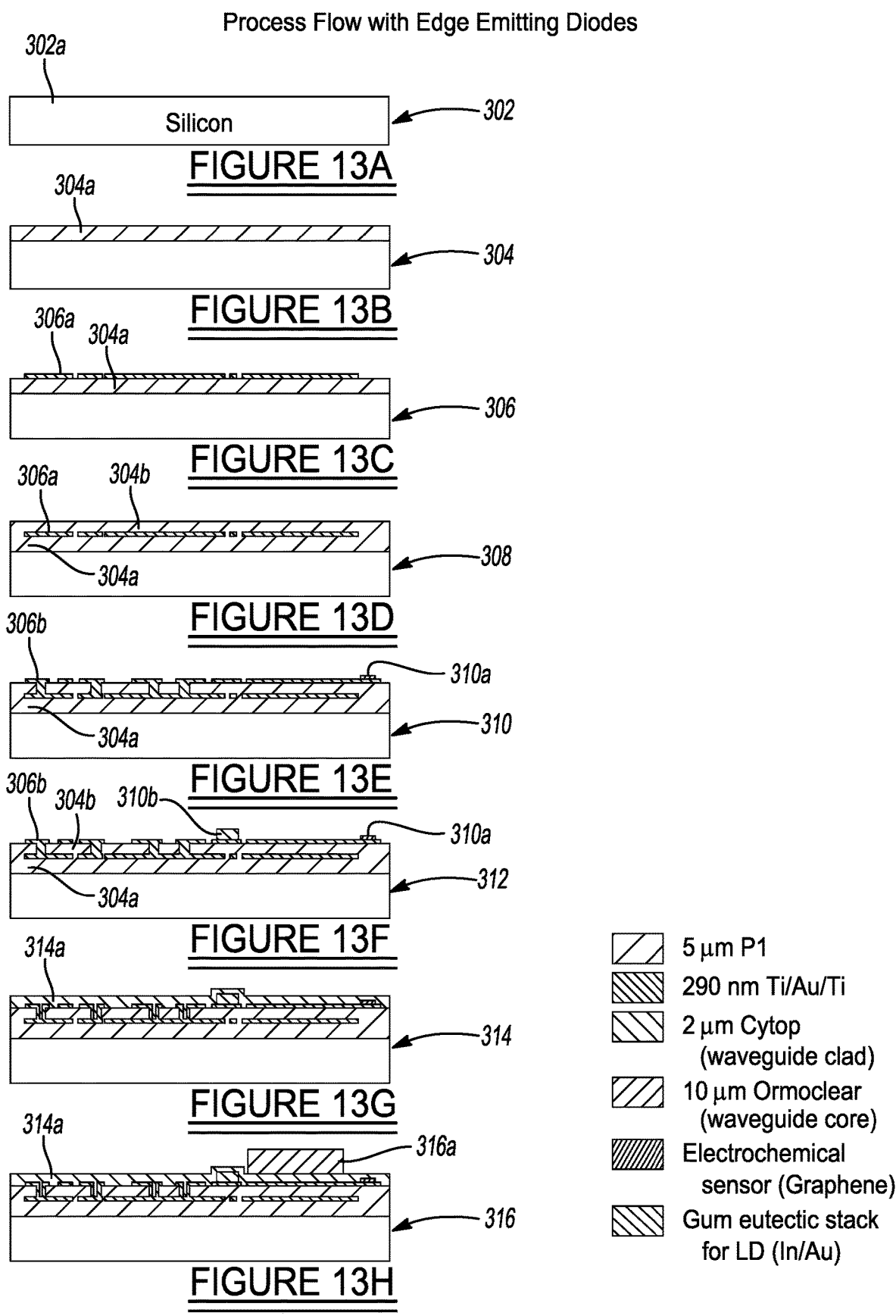

Process Flow with Edge Emitting Diodes

Legend:
- 5 µm P1
- 290 nm Ti/Au/Ti
- 2 µm Cytop (waveguide clad)
- 10 µm Ormoclear (waveguide core)
- Electrochemical sensor (Graphene)
- Gum eutectic stack for LD (In/Au)

SYSTEMS AND METHODS FOR FLEXIBLE, HIGH-DENSITY OPTO-ELECTRONIC ARRAYS

STATEMENT OF GOVERNMENT RIGHTS

The United States Government has rights in this invention pursuant to Contract No. DE-AC52-07NA27344 between the U.S. Department of Energy and Lawrence Livermore National Security, LLC, for the operation of Lawrence Livermore National Laboratory.

FIELD

The present disclosure relates to probes and electrode systems and methods for monitoring electrical signals, and more particularly to a high density, opto-electronic array having a portion which is implantable into an anatomy, and which is especially well suited for bioengineering applications.

BACKGROUND

The statements in this section merely provide background information related to the present disclosure and may not constitute prior art.

Bioengineering applications, and particularly those involving neural implants, can involve collecting neural responses from dozens, hundreds or even thousands or more individual electrodes, or applying electrical or optical signals to the human body, and particularly the brain, via a corresponding large number of electrodes.

As the need for recording electrical activity in bioengineering applications has increased in recent years, so too has the number of electrodes needed to accomplish the necessary recording. The issue becomes especially acute when tens of thousands of electrodes are needed to collect and transmit information to some subsystem for recording. Under this circumstance, the traditional approach of using individual electrical conductors to make contact with separate electrodes, and separate electrical conductors to route signals from each electrode to various electronics and signal conditioning components, becomes extremely unwieldly and impractical. This is because such existing systems are based on an electrical processing interface which has to connect to the wires associated with each one of the electrodes. As the number of electrodes increases so does the corresponding number of independent wires that need to be incorporated and interfaced to other electronic components. The electrical interface which connects the wires to associated electronics, such as amplifiers, signal conditioning and other electronic components, becomes a limiting factor when hundreds, thousands or more independent wires need to be interfaced to one or more electronic amplifiers and other electronic components. In particular applications, such as bioengineering applications, the electrode arrays typically need to be small and easily implantable or capable of being carried on the person of an individual. This becomes virtually impossible as hundreds, thousands or more independent electrodes are used and as the electrical interface needed becomes larger and more complex. In effect, the resulting interface must grow in dimensions to accommodate the needed wiring and electrical connections between the electrodes and associated electronics. These limitations constrain the number of electrodes that can be used in applications where space is limited. Large numbers of independent wires and the lengths of wiring used can also have negative effects of parasitic capacitance and may lead to less than optimal signal quality of the received signals from the electrodes.

Accordingly, there is a strong need in many applications, and particularly in the bioengineering field in connection with neural monitoring and stimulation applications, for microelectrode arrays which enable interfacing to extremely large pluralities of electrodes (e.g., hundreds, thousands or more), more efficiently and with more compact subassemblies that minimize or eliminate the need for point to point wiring connections and independent wires.

SUMMARY

This section provides a general summary of the disclosure, and is not a comprehensive disclosure of its full scope or all of its features.

In one aspect the present disclosure relates to an opto-electronic probe system. The probe system may comprise a probe element including at least one microelectrode. The probe element is implantable in an anatomy to receive electrical signals generated within the anatomy. The probe system further includes a subsystem for at least one of generating excitation signals to be used in stimulating the anatomy, or for receiving electrical signals received from the anatomy. The probe system further includes an interface portion in communication with the subsystem for communicating at least one of electrical signals or optical signals indicative of the electrical signals received by the microelectrode.

In another aspect the present disclosure relates to an opto-electronic probe system. The probe system may comprise a probe element configured for implantation into an anatomy. The probe element may include an electronics subsystem including an array of integrated microelectrodes for receiving electrical signals originating from within the anatomy. The probe element may also include an optical subsystem in communication with the electronic subsystem for receiving the electrical signals and converting the electrical signals to optical signals. An interface subsystem may also be included which has an optical waveguide assembly coupled to the probe element for transmitting the optical signals to a remote subsystem.

In another aspect the present disclosure relates to an opto-electronic probe system which may comprise an interface subsystem having: an electro-optical subsystem configured to generate an optical excitation signal to be applied to a portion of an anatomy, and for receiving electrical signals back from the anatomy in response to an application of the optical signal; an optical waveguide for receiving the optical excitation signal; and at least one electrical conductor for receiving electrical signals. The probe system may also include a probe element in communication with the interface subsystem, with at least a segment of the probe element being implantable in the tissue. The probe element may include an optical element for directing the optical excitation signal into the anatomy, and at least one microelectrode for receiving the electrical signals emanating from within the anatomy and transmitting the electrical signals to the electrical conductor of the interface subsystem.

In still another aspect the present disclosure relates to a method for detecting electrical signals emanating from within an anatomy. The method may comprise using an implantable probe element having at least one microelectrode configured to receive signals emanating from within the anatomy. The method may further comprise using a subsystem to at least one of generate an optical excitation signal applied to the anatomy, or to receive the signals collected by the microelectrode. The method may further involve using an interface subsystem to communicate at least one of electrical signals or optical signals from the probe element to a remote subsystem.

Further areas of applicability will become apparent from the description provided herein. It should be understood that the description and specific examples are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings, in which:

FIG. 1 is a high level block diagram of the components included in one embodiment of a probe system in accordance with the present disclosure;

FIG. 1A is a high level block diagram showing another embodiment of an electronics subsystem portion of the probe of FIG. 1 in which the electronics subsystem makes use of a VCSEL that both converts electrical output signals into optical output signals, and also supplies an optical excitation signal into the tissue in which the probe element of FIG. 1 is implanted;

FIG. 2 is a perspective view of one embodiment of the integrated microelectrode of FIG. 1, which in this example makes use of a vertical cavity surface emitting laser (VCSEL) to help form an optical interface with a plurality of electrodes carried on the device;

FIG. 3 is a side view schematic representation of the integrated microelectrode of FIG. 2 more fully illustrating the various material layers and components used in its construction and a flexible optical waveguide assembly used to interface the device to a remotely located opto-electronics subsystem;

FIG. 4 is a highly enlarged perspective view of one end of the integrated microelectrode shown in FIG. 3 showing certain of the subcomponents thereof;

FIGS. 6A-6l are a series of side view schematic illustrations illustrating a sequence of manufacturing and assembly of the various materials and components of the integrated microelectrode array of FIG. 3;

FIG. 7 is a side view of an another embodiment of an integrated microelectrode probe of the present disclosure which makes use of edge emitting diodes to help form an optical interface portion of the device, and which operates to send an optical excitation signal into tissue while simultaneously receiving electrical signals generated from within the tissue;

FIG. 8 is a highly enlarged plan view of just an end portion of the probe of FIG. 7;

FIG. 9 is a highly enlarged plan view of just a portion of the end of the probe shown in FIG. 8;

FIG. 10 is a highly enlarged plan view of just an outer most tip portion of the end of the probe more fully illustrating one example of an arrangement of electrodes at the outermost tip portion;

FIG. 11 is a plan view of an alternative arrangement for the electrodes at the outermost tip portion of the probe;

FIG. 12 is a plan view of yet another alternative arrangement of the electrodes at the outermost tip portion of the probe.

DETAILED DESCRIPTION

Figure 5:
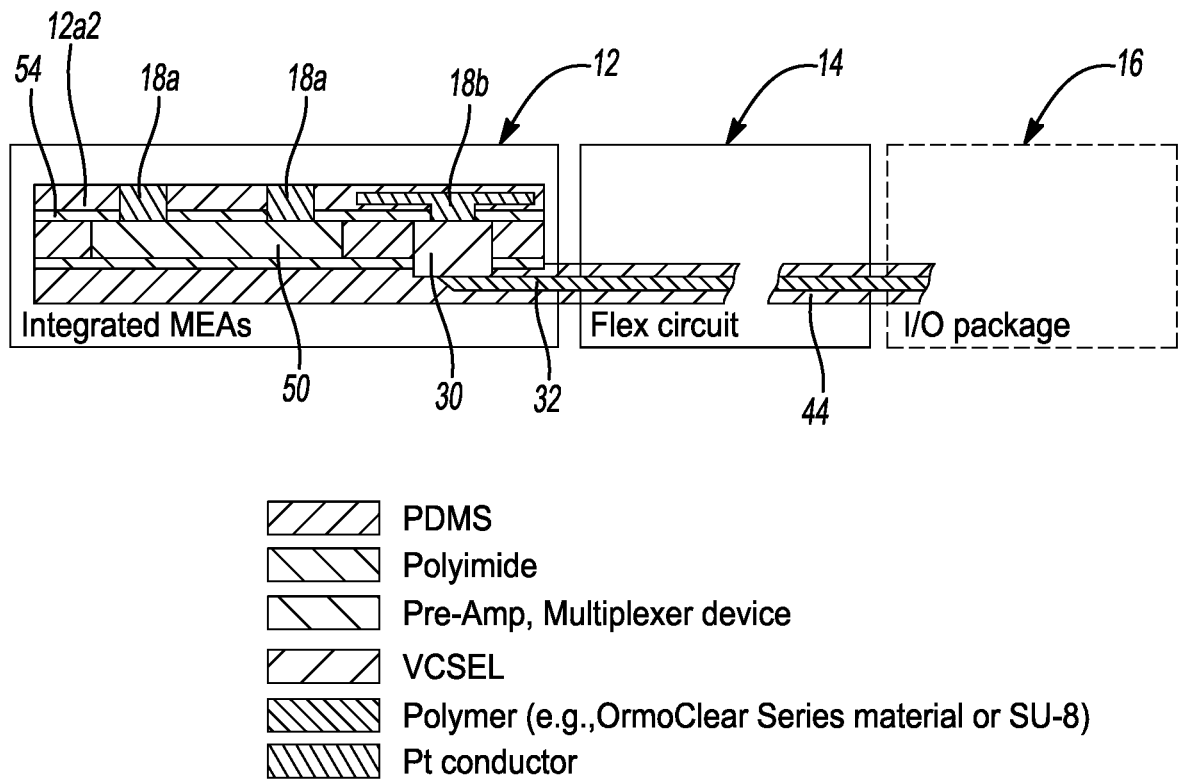
FIG. 5 is a highly enlarged section of just the optical interface portion of the integrated microelectrode of FIG. 3.

Example embodiments will now be described more fully with reference to the accompanying drawings.

Referring to FIG. 1 there is shown a high level block diagram of an integrated microelectrode probe system 10 (hereinafter simply "probe" 10) in accordance with the present disclosure. The probe 10 in this example may include a probe element 12 having an electronics subsystem 13 which communicates with, and which is more preferably connected to, a flexible component 14. The flexible component 14 in this example comprises a flexible optical/electrical interface circuit (hereinafter simply "flexible interface circuit" 14). The flexible interface circuit 14 in turn communicates with a remote I/O subsystem 16 for supplying DC power received from the remote I/O subsystem 16 to the probe element 12, and also passes optical signals received from the probe element 12 to the remote I/O subsystem.

The electronics subsystem 13 in this example is carried on a flexible substrate 12a and enables the probe element 12 to be easily implanted in tissue of an anatomy. In one example implementation the anatomy is a human anatomy, and in one specific implementation the anatomy is a human brain. However, the probe element 12 may be implemented in anatomy, human or animal, where it is desired to monitor electrical signals emanating from the tissue of the anatomy or even to provide electrical signals that stimulate the tissue.

The electronics subsystem 13 in FIG. 1 may include a plurality of microelectrodes 18a arranged in one or more distinct arrays 18, a corresponding plurality of preamplifiers 20 (e.g., one for each microelectrode 18a), and a multiplexer circuit 22 in communication with the preamplifiers 20. A digital driver circuit 26 or an analog driver circuit 28, or even potentially both types of driver circuits 26 and 28, may be incorporated to receive electrical signals from the multiplexer circuit 22. If the digital driver circuit 26 is incorporated, then an analog to digital converter circuit 24 may be included as well to convert analog signal from the multiplexer circuit to corresponding digital output signals. The electrical output signals provided by either the digital driver circuit 26 or the analog driver circuit 28 are used to drive a laser module or subsystem 30, which in one embodiment may be a VCSEL (Vertical Cavity Surface Emitting Laser) subsystem (for convenience hereinafter referred to as "VCSEL subsystem" 30). Potentially other forms of laser subsystem, and as one example diode lasers, may be used in place of the VCSEL, and thus the present disclosure is not limited to use with any one specific form of laser.

In some embodiments the electronics system 13 may include a battery 19, in one example a rechargeable DC battery, for powering the various components of the probe element 12. The electronics subsystem 13 may also optionally include a wireless protocol communications subsystem 21. The wireless protocol communication subsystem 21 may comprise a BLUETOOTH® protocol communications subsystem (i.e., BLUETOOTH® protocol radio), a ZIGBEE® protocol communications subsystem, an IRDA® wireless communications protocol subsystem, or any other type of wireless communications protocol system.

The VCSEL subsystem 30 may be used to convert (i.e., transduce) the electrical signals detected by the microelectrodes 18a, which are transmitted by the electronics subsystem 13 to the VCSEL subsystem 30, into corresponding optical signals. The optical signals are transmitted from the VCSEL 30 over an optical waveguide 32. The optical waveguide 32 in this example is formed on a substrate 34 of the flexible interface circuit 14. An electrical conductor 36, in one example a platinum electrical conductor, is also formed on or otherwise secured to the substrate 34. The optical waveguide 32 communicates with an optical output detector circuit 38 and the electrical conductor 36 communicates with a power/clock circuit 40 and optionally with a controller 42. The power/clock circuit 40 may be an independent circuit or it may be combined with the controller 42. The components 38, 40 and 42 are supported on a substrate 44 which may be a rigid substrate or a flexible substrate. The electrical conductor 36 may communicate via a bus 46 or a bus 48, with the multiplexer 22 and the preamplifiers 20, as well as either one or both of the digital driver circuit 26 and the analog driver circuit 28.

Referring to FIGS. 2 and 3, the probe 10 construction can be seen in greater detail. In this example the probe element 12 may comprise a PDMA (Plastic Deformation Magnetic Assembly) microstructure where the substrate 12a is made in part from PDMS (polydimethylsiloxane). The substrate 12a encases a plurality of integrated circuit (IC) sections 50 each having a plurality of parallel arranged microelectrodes 18a thereon. The IC sections 50 may include the multiplexers 22 and the preamplifiers 20 needed to communicate and condition the signals from the microelectrodes 18a associated therewith. The microelectrodes 18a may be formed in part by Platinum or any other suitably electrically responsive material. The microelectrodes 18a in this example are spaced apart longitudinally in line along a length of each one of the IC sections 50, although other arrangements of the microelectrodes 18a are possible, and the precise arrangement of the microelectrodes may depend at least in part on the final shape of the probe element 12 and/or the portion of anatomy that the probe element 12 is expected to be implanted in.

FIGS. 2 and 4 illustrate the flexible interface circuit 14 in this embodiment as a coiled assembly, although it need not be coiled. The substrate 44 in this example may also be made from PDMS and the optical waveguide 32 is formed, in one example, from an epoxy-based negative photoresist, for example ORMOCLEAR™ material or optionally from SU-8. This construction provides the flexible interface circuit 14 with its ability to flex, bend and/or be coiled, which provides added flexibility in coupling the probe element 12 to the I/O subsystem 16. FIG. 4 illustrates the VCSEL 30 being in electrical communication with the IC section 50 via a short length 12a1 of the PDMS substrate 12a.

FIG. 5 provides a more detailed, high level side cross-sectional view of the arrangement of the material layers of the probe element 12 and the flexible interface circuit 14. The probe element 12 microelectrodes 18a can be seen to be mostly encased within the substrate layer 12a of PDMS. The microelectrodes 18a extend through a polymer layer 54, in this example a polyimide layer, which forms a moisture and dielectric barrier. The microelectrodes 18a extend into contact with one of the IC sections 50, which is in turn encased within the polymer layer 54. The VCSEL subsystem 30 is in contact with an additional conductive section 18b, which supplies an output signal from the IC section 50 to the VCSEL subsystem. The VCSEL subsystem 30 is supported adjacent one end of the optical waveguide 32, and in this example the distal end is encapsulated within PDMS substrate 12a material.

FIGS. 6A-6L illustrate a series of high level side view of material sections showing a sequence of operations that may be used to form the probe element 12 and the flexible interface circuit 14 in a layer-by-layer sequence. It will be appreciated that other materials may be substituted for those specifically mentioned in the following discussion below, and as such the construction is not limited to only those specific materials mentioned.

At operation "A" a layer 102 of PDMS may be formed or deposited on a layer 100 of silicon. At operation "B" a polymer layer 104 (e.g., OROMOCLEAR™ material, or SU-8 material, etc.) may be formed or deposited on a section of the PDMS layer 102. At operation "C" an additional layer of PDMS 106 may be applied over the polymer layer 104. At operation "D", discrete sections of polyimide 108 may be applied over portions of the PDMS layer 106. At operation "E", additional layers of polyimide 110 are applied over the polyimide layers 108. At operation "F", the VCSEL 30 is formed or fabricated in contact with the polymer layer 104 (where layer 104 forms the optical waveguide 32), and the electronics IC section 50 is fabricated or applied on the polyimide layer 108. At operation "G" addition layers of polyimide 112 are formed over portions of the IC section 50, the VCSEL 30 and the PDMS layer 110. At operation "H", additional layers 114 of PDMS are formed on the polyimide layers 112. At operation "I" metallic layers 116 are formed so as to be in contact with the integrated IC 50 and the VCSEL subsystem 30. Metallic layer portions 116 thus form the microelectrodes 18a. At operation "J" additional layers of PDMS 117 are applied to at least partially encapsulate the metallic layer portions 116. At operation K" additional layers of metallic material 118 may be applied such that portions of the metallic material form exposed pads at an upper surface. The finished probe system 10 is shown at "J" with the silicon layer 100 removed.

FIG. 1A shows a probe element 12' in accordance with another embodiment of the present disclosure. In this example the probe element 12' is constructed similarly to the probe element 12, although the probe element 12' also includes an optical waveguide element 15 which receives an optical excitation signal from the VCSEL subsystem 30 and transmits the optical excitation signal into the tissue in which the probe element 12' is implanted. Accordingly, in this embodiment the VCSEL subsystem 30 is used to both output an optical signal in accordance with the detected electrical signals, as well as to supply an optical excitation signal. Optionally, a second VCSEL subsystem or even one or more edge emitting diodes may be used to supply the excitation signal. In either instance, the probe element 12' carries out the dual function of both providing an optical excitation signal as well as detecting and collecting the electrical signals emanating from within the tissue as a result of the stimulation.

FIG. 7 shows a probe system 200 in accordance with another embodiment of the present disclosure. The probe system 200 in this embodiment includes an interface subsystem 202 having an enlarged interface circuit 205, and at least one probe element 204a at a distal end of the interface subsystem 202. The enlarged interface circuit 205 may form an interface with an external subsystem and optionally may include one or more electronic subsystems 205a that provide interfacing, memory (RAM or ROM) and/or processing capabilities. The enlarged interface circuit 205 may also optionally include either or both of a battery 205*b* and a wireless communications subsystem 205*c*.

As shown in FIG. 8, the interface subsystem 202 includes a pair of neck portions 202*a* that terminate at a pair of independent distal probe elements 204*a*. Each of the distal probe elements 204*a* is configured to be implanted in anatomical tissue. While two neck portions 202*a* are shown, it will be appreciated that a greater or lesser plurality of neck portions 202*a* may be included to meet the needs of a specific application. Accordingly, the interface subsystem 202 is not limited to an implementation with any specific number of neck portions.

FIG. 9 shows an enlarged area of the interface subsystem 202 which includes an opto-electronics circuit portion 204*b* having electronic integrated circuit components 206 and optical elements 208*a*. The optical elements 208*a* in this example each comprise edge emitting diodes, and will be referred to as such throughout the following discussion. The edge emitting diodes 208*a* transmit optical signals down optical waveguide portions 210*a* supported on the two adjacent neck portions 202*a* of the interface subsystem 202 to the probe elements 204*a*. Portions of each of the optical waveguide portions 210*a* extend onto the probe elements 204*a*. One of the probe elements 204*a* is shown in highly enlarged fashion in FIG. 10. The neck portions 202*a* form two independent elements which communicate independently with their respective probe elements 204*a* of the probe 200. In this example the neck portions 202*a* are constructed identical to one another, but they need not be identical.

FIG. 10 also shows the probe element 204*a* including a plurality of electrical circuit traces 214*a*, one each being associated with a specific one of a plurality of microelectrodes 216*a*1-216*a*8. In this example eight microelectrodes 216*a*1-216*a*8 are included, although a greater or lesser number of independent microelectrodes may be used to meet the needs of a particular application. The probe elements 204*a* in this example are constructed in identical fashion, but they need to be constructed identically. As such, they may differ slightly in construction from one another, such as for example having different numbers of microelectrodes and/or different shapes. For the present discussion, however, it will be assumed that the probe elements 204*a* are identical in construction.

In FIG. 10 the microelectrodes 216*a*1-216*a*8 are illustrated as being arranged in a straight line along a longitudinal mid-point of the probe element 204*a*. FIG. 11 shows another configuration where the microelectrodes 216*a*1-216*a*8 are arranged in two parallel, linearly arranged groups of four each. FIG. 12 shows still another configuration where the microelectrodes 216*a*1-216*a*8 are arranged in a straight line but aligned longitudinally with their respective optical waveguide 210*a*. It will be appreciated that the microelectrodes 216 may be arranged in other patterns as well to accommodate a specific application.

In all of the above configurations, the optical excitation signals passing through the optical waveguides 210*a* are emitted into tissue in the anatomical area in which the probe elements 204*a* are implanted. The emitted optical excitation signals may produce (or enhance) the generation of electricals signals within the tissue. The electrical signals generated within the tissue are detected by the microelectrodes 216*a*1-216*a*8 and fed back via the circuit traces 214*a* to the interface subsystem 202 of the probe system 200. The interface subsystem 202, and particularly its enlarged interface circuit 205, may be connected to any suitable type of connector so that the electrical signals can be output to one or more remote electronic analysis/recording subsystems. Such subsystems, if sufficiently small, may even be carried on the person of an individual.

Figure 13I:
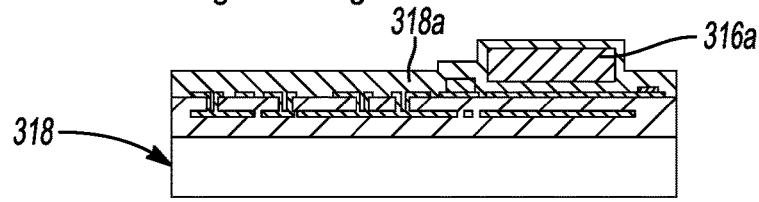
FIGS. 13A-13O is a series of simplified schematic side view illustrations representing operations in constructing the probe of FIG. 7.
Figure 13J:
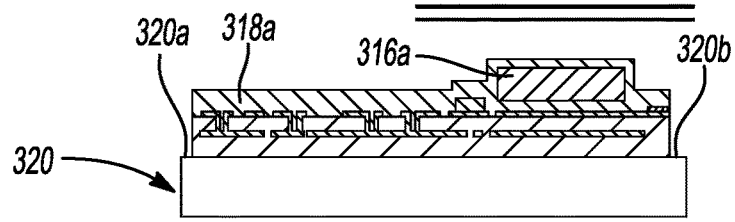
Figure 13K:
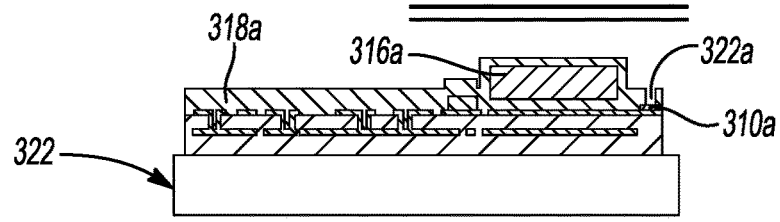
Figure 13L:
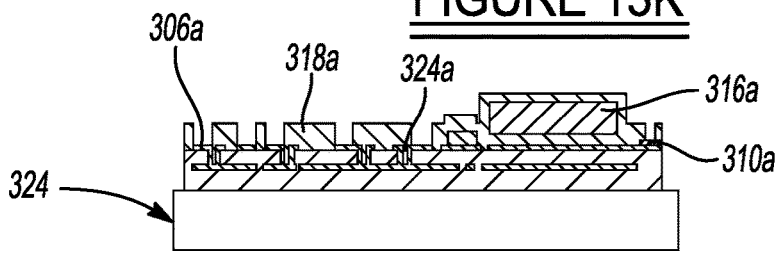
Figure 13M:
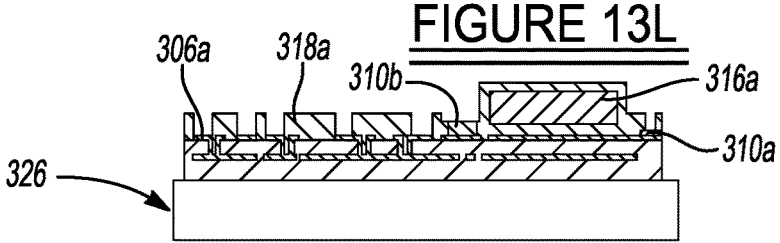
Figure 13N:
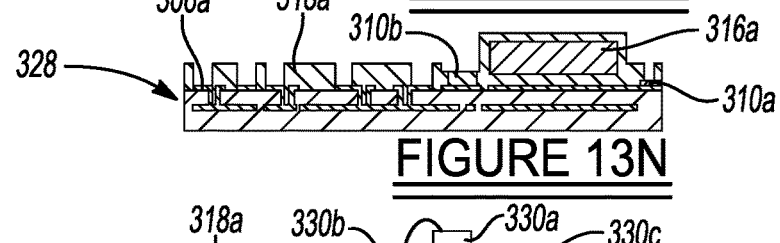
Figure 13O:
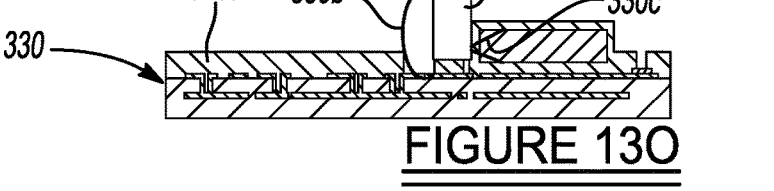

Referring to FIGS. 13A-13O, a series of illustrations representing various manufacturing operations are presented to illustrate one example of how the probe system 200 may be manufactured. At operation 302 the manufacture may begin with providing a silicon substrate layer 302*a*. At operation 304 a layer of Palladium 304*a*, for example 5 um thick, may be formed on the silicon substrate. At operation 306 discrete sections of a thin layer of Ti/Au/Ti 306*a* may be formed or deposited on the Palladium layer 304*a*. At operation 308 an additional layer of Palladium 304*b* is applied over the Ti/Au/Ti layer sections 306*a*. At operation 310, additional sections of Ti/Au/Ti material 306*b* may be added to communicate with the layer 306*a*, and electromechanical sensor material (e.g., Graphene) 310*a* may be added to or formed on a portion of the layer 306*b*. Also, eutectic metal stack (In/Au gold in this implementation) 310*b* forming a metal bonding pad for lasers may be added at operation 310*b*.

At operation 314 a waveguide cladding material layer 314*a* (e.g., 2 um CYTOP™ amorphous fluoropolymer material) may be formed or deposited on over the entire upper surface of the assembly. At operation 316 a waveguide core 316*a* (e.g., 10 um ORMOCLEAR™ material) may be formed or deposited on a portion of the waveguide cladding material layer 314*a*. At operation 318 another layer of waveguide cladding material 318*a* may be formed or deposited over the entire surface of the assembly. At operation 320 portions of the entire subassembly of layers may be removed to expose the Silicon at opposing ends 320*a* and 320*b* of the substrate. At operation 322 a section of the waveguide cladding material layer 318*a* may be removed to expose the electrochemical sensor material 310*a*.

Referring further to FIG. 13L, at operation 324 portions 324*a* of the waveguide cladding material layer 318*a* removed to expose sections of the thin layer of Ti/Au/Ti 306*a*. At operation 326 an additional portion of the top cladding layer 318*a* may be removed to expose the Eutectic stack material 310*b*. At operation 328 the Silicon substrate 302*a* is removed. At operation 330, edge-emitting laser diode 330*a* is flipchipped. The diode is wirebonded at 330*b* and tested for lasing at 330*c*.

It will be appreciated that for each of the embodiments described herein, the materials used may be flexible or non-flexible. With regard to FIGS. 5, 6A-6L and 13A-13O, while specific materials have been mentioned in the construction of the probe element 12 and the probe system 200, it will be understood that the materials mentioned are only intended to be examples of suitable materials, and those skilled in the art will recognize that a wide range of other materials may be included in constructing the various embodiments described herein.

The present disclosure thus provides various embodiments of probe systems that may be used to collect electrical signals and convert same to optical signals, to facilitate the integration of much more densely packaged microelectrode arrays, as well as to apply optical signals to help stimulate a selected area of tissue. The various embodiments enable hundreds, thousands or more microelectrode arrays to be implemented without the limitations present when electrical conductors are used to interface the microelectrodes to external recording subsystems. The electro-optical interface embodiments described herein are expected to significantly expand the use of bioengineering probes as well as facilitate easier implementation of complex probes into delicate areas of the human anatomy, and particularly into the human brain.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

What is claimed is:

1. An opto-electronic probe system comprising:
   a probe element configured for implantation in an anatomy and configured to receive electrical signals generated within the anatomy;
   an electronics subsystem located on the probe element, for at least one of generating excitation signals configured to be used in stimulating the anatomy, or configured for receiving electrical signals received from the anatomy, the electronics subsystem including at least one electronic circuit, at least one laser subsystem and at least one microelectrode configured on a common substrate, for at least one of generating the excitation signals into the anatomy or receiving the electrical signals from the anatomy;
   a remote input/output (I/O) subsystem for generating electrical control signals;
   an interface portion forming a flexible interface circuit and being in communication with the electronics subsystem and the remote I/O subsystem, and having an electrical bus and an optical waveguide supported thereon, the electrical bus configured to communicate the electrical control signals to the electronic circuit, and for helping to control the microelectrode, and the interface portion further configured for communicating optical signals, indicative of the electrical signals received by the microelectrode, to the remote I/O subsystem; and
   wherein the electronics subsystem is located at a first end of the interface portion and the remote input/output (I/O) is located at a second, opposite end of the interface portion.

2. The system of claim 1, wherein the microelectrode comprises an integrated array of microelectrodes, arranged in a cylindrical arrangement, for receiving electrical signals originating from within the anatomy.

3. The system of claim 2, wherein ones of the integrated array of microelectrodes are arranged around a circumference of the probe element in a configuration of a plurality of linear strips.

4. The system of claim 1, wherein the laser subsystem is configured to generate the optical signals over the interface portion.

5. The system of claim 4, wherein the laser subsystem comprises a vertical cavity surface emitting laser subsystem.

6. The system of claim 4, wherein the electronics subsystem comprises the laser subsystem and electronics circuits, the electronics circuits being in communication with the microelectrode and generating electrical output signals for driving the laser subsystem.

7. The system of claim 4, wherein the laser subsystem is configured to convert the electrical signals received by the microelectrode to optical signals for transmission over the interface portion.

8. The system of claim 4, wherein the probe element further includes an optical waveguide, and wherein the laser subsystem is used to generate an optical signal which is carried by the optical waveguide into the anatomy.

9. The system of claim 4, wherein the laser subsystem comprises at least one edge emitting diode for generating an optical signal applied to the probe element and configured to be transmitted into the anatomy.

10. The system of claim 1, wherein the interface portion comprises a flexible component having a waveguide assembly for transmitting the optical signals to the remote I/O subsystem.

11. The system of claim 1, wherein the interface portion comprises both an optical waveguide and at least one electrically conductive circuit trace for communicating both optical and electrical signals between the probe element and the remote I/O subsystem.

12. The system of claim 1, wherein the electronics subsystem includes a plurality of laser diodes and the interface portion includes a plurality of optical waveguides, each one of the plurality of laser diodes communicating with an associated one of the optical waveguides and generating optical excitation signals passed over the plurality of optical waveguides to the probe element.

13. The system of claim 12, wherein the laser diodes each comprise edge emitting laser diodes.

14. The system of claim 12, wherein the probe element comprises first and second independent probe elements in communication with the separate waveguides and with the interface portion, and wherein each of the first and second independent probe elements includes at least one said microelectrode, and wherein portions of the separate waveguides extend onto each one of the first and second independent probe elements.

15. The system of claim 14, wherein the each one of the first and second independent probe elements includes:
an array of microelectrodes; and
the electronics subsystem comprises an optical source carried on the interface portion for generating an optical excitation signal, the optical excitation signal being transmitted over the separate waveguides.

16. An opto-electronic probe system comprising:
a probe element configured for implantation into an anatomy, the probe element including:
an electronics subsystem including a laser subsystem and an array of integrated microelectrodes configured for receiving electrical signals originating from within the anatomy, and arranged on a common substrate of the probe element to be spaced apart in three dimensions on the probe element; and
the laser subsystem configured to be in communication with the electronics subsystem for receiving the electrical signals and converting the electrical signals to optical signals;
a remote input/output (I/O) subsystem including a clock, for supplying power and electrical control signals to the electronics subsystem; and
an interface subsystem forming a flexible interface circuit and having an optical waveguide assembly and an electrical bus, coupled to the probe element, for transmitting the optical signals received from the laser subsystem to the remote I/O subsystem, and for receiving the power and electrical control signals from the remote I/O subsystem and transmitting the power and electrical control signals to the electronics subsystem; and
wherein the electronics subsystem is arranged at a first end of the interface subsystem and the remote input/output (I/O) subsystem is arranged at a second end of the interface subsystem opposite to the first end.

17. The system of claim 16, wherein the laser subsystem comprises a vertical cavity surface emitting laser (VCSEL).

18. The system of claim 16, further comprising an additional waveguide supported on the probe element and in communication with the optical subsystem, and wherein the optical subsystem comprises a laser module, and wherein the laser module is configured to supply an optical excitation signal to the additional waveguide which is directed into the anatomy via the additional waveguide.

19. An opto-electronic probe system comprising:
an interface subsystem including:
an interface circuit forming an interface with an external subsystem, and including an opto-electronics circuit portion including an integrated circuit component and an optical signal generating component and, wherein the optical signal generating component is configured to generate an optical excitation signal, the optical excitation signal configured to be applied to a portion of an anatomy, and the opto-electronics circuit portion further configured to receive electrical signals back from the anatomy in response to an application of the optical excitation signal;
an elongated neck portion forming a signal transmission element in communication with the interface circuit, the interface circuit being configured at a first end of the neck portion, at least a segment of the neck portion being configured for implantation in the portion of the anatomy, and the neck portion including:
an optical waveguide extending along a first portion of a length of the neck portion;
an optical probe element disposed at a distal second end of the neck portion opposite to the first end and in communication with the optical waveguide, and configured to direct the optical excitation signal into the portion of the anatomy;
an electrical circuit trace extending along a second portion of the length of the neck portion adjacent to the optical waveguide, and into the optical probe element;
the optical probe element further including at least one microelectrode also disposed at the distal end of the neck portion adjacent a distal end of the optical waveguide, and in communication with the electrical circuit trace, and configured to receive the electrical signals emanating from within the portion of the anatomy in response to the optical excitation signal being directed into the portion of the anatomy, and to transmit the received electrical signals to the opto-electronics circuit portion of the interface subsystem.

20. The system of claim 19, wherein the optical signal generating component includes a laser diode for generating the optical excitation signal.

21. The system of claim 19, wherein the interface subsystem includes first and second independent neck portions each having an array of microelectrodes.

22. The system of claim 21, wherein each one of the neck portions includes separate first and second waveguide elements.

23. A method for detecting electrical signals emanating from within an anatomy, the method comprising:
  using an implantable probe element having an electronics circuit, a laser subsystem and at least one microelectrode all configured on a common substrate, wherein the microelectrode is configured to receive signals emanating from within the anatomy;
  using a subsystem mounted on the implantable probe to at least one of:
    generate an optical excitation signal applied to the anatomy, or
    to receive the signals collected by the microelectrode;
  using a remote electronic input/output (I/O) subsystem configured to supply electrical control signals for use in helping to control the electronics circuit of the probe element;
  using an interface subsystem forming a flexible interface circuit configured to be interfaced at opposite ends to the implantable probe and the remote I/O subsystem, to communicate electrical control signals to the implantable probe, as well as to receive optical signals from the probe element and to transmit the received optical signals to the remote I/O subsystem, the electrical control signals being received from the remote I/O subsystem.

* * * * *